United States Patent
Xu et al.

(10) Patent No.: US 7,557,060 B2
(45) Date of Patent: Jul. 7, 2009

(54) SOLID PHOSPHORIC ACID WITH CONTROLLED POROSITY

(75) Inventors: Ling Xu, Louisville, KY (US); Wayne Turbeville, Crestwood, KY (US); Gregory A. Korynta, Louisville, KY (US); Jeffrey L. Braden, New Albany, IN (US)

(73) Assignee: Sud-Chemie Inc., Louisville, KY (US)

( * ) Notice: Subject to any disclaimer, the term of this patent is extended or adjusted under 35 U.S.C. 154(b) by 0 days.

(21) Appl. No.: 11/770,767

(22) Filed: Jun. 29, 2007

(65) Prior Publication Data

US 2009/0005623 A1 Jan. 1, 2009

(51) Int. Cl.
*B01J 27/00* (2006.01)
*B01J 27/182* (2006.01)
*B01J 21/00* (2006.01)
*C01B 15/16* (2006.01)
*C01B 25/26* (2006.01)
*C07C 2/02* (2006.01)
*C07C 6/12* (2006.01)
*C07C 13/28* (2006.01)
*C07C 2/64* (2006.01)
*C07C 15/067* (2006.01)

(52) U.S. Cl. .................. 502/208; 502/214; 502/232; 423/308; 423/309; 423/311; 585/422; 585/446; 585/502

(58) Field of Classification Search .......... 502/208, 502/214, 232; 423/308, 309, 311; 585/422, 585/446, 502
See application file for complete search history.

(56) References Cited

U.S. PATENT DOCUMENTS

| | | | |
|---|---|---|---|
| 1,993,513 A | 3/1935 | Ipatieff | |
| 3,044,964 A * | 7/1962 | Morrell | 502/64 |
| 3,112,350 A | 11/1963 | Bielawski et al. | |
| 3,661,801 A | 5/1972 | Gutmann et al. | |
| 3,758,627 A * | 9/1973 | Juguin et al. | 585/514 |
| 4,619,908 A | 10/1986 | Cheng et al. | |
| 4,912,279 A * | 3/1990 | Wilcher et al. | 585/466 |
| 4,946,815 A * | 8/1990 | Chao et al. | 502/81 |
| 5,043,509 A * | 8/1991 | Imai et al. | 585/466 |
| 5,059,737 A * | 10/1991 | Chao et al. | 585/466 |
| 5,081,086 A * | 1/1992 | Wilcher et al. | 502/81 |
| 5,177,283 A * | 1/1993 | Ward | 585/446 |
| 6,040,262 A * | 3/2000 | Fougret et al. | 502/162 |

FOREIGN PATENT DOCUMENTS

| | | | |
|---|---|---|---|
| EP | 0 371 938 A1 | | 6/1990 |
| EP | 0 447 705 | * | 9/1991 |
| EP | 0 570 070 B1 | | 11/1993 |

OTHER PUBLICATIONS

"An improved solid phosphoric acid catalyst for alkene oligomerization in a Fischer-Tropsch refinery," Johannes H. Coetzee et al. Applied Catalysis A: General 308 (2008), pp. 204-209.*

"Solid Phosphoric Acid Catalyst: A Multinuclear NMR and Theoretical Study," Thomas R. Krawietz, et al. J. Am. Chem. Soc., 1998, 120 (33), pp. 8502-8511.*

* cited by examiner

*Primary Examiner*—Patricia L Hailey

(57) ABSTRACT

The present invention relates to a solid phosphoric acid catalyst and a process for conversion of hydrocarbons using a solid phosphoric acid catalyst. The solid phosphoric acid catalyst comprises silicon orthophosphate, and has a silicon orthophosphate to silicon pyrophosphate ratio of at least about 5:1. The total pore volume of the solid phosphoric acid catalyst is at least about 0.17 cm$^3$ per gram of catalyst, of which at least about 0.15 cm$^3$ per gram is contributed by pores with diameter of at least about 10,000 Å.

18 Claims, No Drawings

SOLID PHOSPHORIC ACID WITH CONTROLLED POROSITY

BACKGROUND

This invention relates to a solid phosphoric acid (SPA) catalyst comprising silicon orthophosphate and optionally silicon pyrophosphate. The catalyst is characterized by a pore volume of at least about 0.17 cm$^3$ g$^{-1}$, of which at least about 0.15 cm$^3$ g$^{-1}$ is due to macropores with diameters greater than about 10,000 Å. The integrated XRD reflectance intensity ratio of silicon orthophosphate to silicon pyrophosphate, if the latter is present, is at least about 5:1 and preferably at least about 8:1.

Solid phosphoric acid catalysts are commonly used in hydrocarbon conversion processes that require a strongly acidic catalyst. Examples of hydrocarbon conversion processes in which solid phosphoric acid catalysts have been used include, without limitation, the oligomerization of light olefins to a mixture of heavier olefins and paraffins ("polymer gasoline" or "polygas") and the alkylation of benzene and other aromatic hydrocarbons with olefins to produce alkyl aromatic products such as cumene and ethylbenzene.

The basic recipe for solid phosphoric acid catalysts is disclosed in U.S. Pat. No. 1,993,513, which discloses a catalyst prepared from 89% aq. phosphoric acid and kieselguhr. A mixture of these two ingredients is calcined and ground down to the desired particle size; the "structure" of the catalyst may be improved by adding an organic binder such as starch or gelatin before calcining. Various improvements on this process have been developed over the years. For example, U.S. Pat. No. 3,112,350 teaches a process in which phosphoric acid of 84.8% P$_2$O$_5$ content is added to diatomaceous earth in an approximately 4:1 ratio. The resulting mixture is extruded, cut into manageable pieces, dried, and calcined.

In very general terms, SPA catalysts comprise a phosphorus source and a silicon source. The phosphorus source, which typically contributes from about 60% to about 80% of the catalyst by weight, is generally some sort of "phosphoric acid." The phosphoric acids are oxyacids of phosphorus in the +5 oxidation state, and have the generic formula H$_{n+2}$P$_n$O$_{3n+1}$. The first three acids in this series are: orthophosphoric acid H$_3$PO$_4$, pyrophosphoric acid H$_4$P$_2$O$_7$, and triphosphoric acid H$_5$P$_3$O$_{10}$. A given sample of "phosphoric acid" will be a mixture of members of the H$_{n+2}$P$_n$O$_{3n+1}$ series and water. The mixture is characterized by the total phosphorus content, which is given as a percentage relative to pure orthophosphoric acid, H$_3$PO$_4$. As the other acids in the series H$_{n+2}$P$_n$O$_{3n+1}$ have a higher phosphorus content (by weight) than orthophosphoric acid, it is not unusual to find phosphoric acids with concentration greater than 100%. Typically, a phosphoric acid of concentration between about 100% and about 120% is used to prepare SPA catalysts.

The silicon source is a siliceous or SiO$_2$-containing material such as kieselguhr, diatomaceous earth, infusorial earth, kaolin, fullers earth, artificially prepared porous silica, or mixtures thereof. Kieselguhr is the most preferred silicon source. However, the terms infusorial earth, kieselguhr, and diatomaceous earth, are often used and referred to interchangeably and on an equivalent basis in general in reference to SPA catalysts.

It is known in the art that the ratio of crystalline phases, i.e. silicon orthophosphate Si$_3$(PO$_4$)$_4$ and silicon pyrophosphate Si$_2$P$_2$O$_7$, in the finished catalyst affects performance. It is also known that the effectiveness of a catalyst is related to the porosity of solid phosphoric acid catalysts. The ratio of crystalline phases may be controlled indirectly by adjusting conditions in the catalyst preparation process, such as the ratio of phosphoric acid to kieselguhr and the calcination temperature. Similarly, the conditions used for the catalyst preparation can effect the finished catalyst porosity.

The term "porosity" as applied to SPA catalysts encompasses both the total pore volume and the distribution of pores of various sizes. The pore size distribution is often described relative to pore volume. That is, a certain percentage of the pore volume is due to, or is contributed by, pores in a certain diameter range: for example, one might say that 80% of the total pore volume is due to pores with diameters >1000 Å. U.S. Pat. No. 3,661,801 teaches a spherical catalyst (not an extrudate) prepared using non-hydrated P$_2$O$_5$ and having between about 0.200 and about 0.400 cm$^3$ g$^{-1}$ of pore volume contributed by pores with diameter >350 Å and between about 0.07 and about 0.20 cm$^3$ g$^{-1}$ of pore volume contributed by pores with diameter >9000 Å. U.S. Pat. No. 5,081,086 teaches a solid phosphoric acid catalyst with a total pore volume of 0.28 cm$^3$ g$^{-1}$ or less, with no more than 25% of the pore volume contributed by pores with diameter >10,000 Å. It is stated in the '086 patent that pores with diameters above 10,000 Å should not contribute a large percentage of the total pore volume, as these large pores are detrimental to the physical strength and longevity of the catalyst. European Patent EP 570,070 B1 teaches a solid phosphoric acid catalyst having an integrated XRD reflectance intensity ratio of silicon orthophosphate to silicon pyrophosphate which is less than about 4:1, and having at least 30% of its total pore volume contributed by pores with diameter >10,000 Å.

In order for the SPA catalysts to function in hydrocarbon conversion processes, the catalysts must have efficient mass transfer and resistance to deactivation, as well as high activity. Toward this end, it would be beneficial to have a SPA catalyst that has an effective ratio of silicon orthophosphate to silicon pyrophosphate, and a pore structure having a sufficient volume of large macropores, with diameters above about 10,000 Å, and preferably above about 50,000 Å.

SUMMARY OF THE INVENTION

It is an object of this invention to provide an improved solid phosphoric acid catalyst for use in hydrocarbon conversion processes and other processes which employ an acid catalyst. The improved catalyst has a higher activity and improved stability with respect to SPA catalysts of the prior art. The catalyst comprises crystalline silicon orthophosphate and, optionally, crystalline silicon pyrophosphate. When both crystalline phases are present, the catalyst has an integrated XRD reflectance intensity ratio of silicon orthophosphate to silicon pyrophosphate of at least about 5:1, and preferably at least about 8:1. The catalyst has a pore volume of at least about 0.17 cm$^3$ g$^{-1}$, of which at least 0.15 cm$^3$ g$^{-1}$ of pore volume which is contributed by pores of diameter >10,000 Å.

It is also an object of this invention to provide a process for converting hydrocarbons using a solid phosphoric acid catalyst having the characteristics described in the previous paragraph. A specific embodiment may be an alkylation process in which benzene and an olefin react to form an alkylbenzene. Another embodiment may be a polygas process, also known as a catalytic condensation process, in which light olefins (having from 2 to about 5 carbons per molecule) are polymerized into hydrocarbons suitable for use in gasoline.

DETAILED DESCRIPTION OF THE INVENTION

The present development is a solid phosphoric acid (SPA) catalyst having an effective ratio of silicon orthophosphate to silicon pyrophosphate, and a pore structure having a sufficient volume of large macropores, with diameters above about 10,000 Å, and preferably above about 50,000 Å. These SPA catalysts may be used in processes for the oligomerization of olefins to polymer gasoline, alkylation of aromatics with olefins to give alkyl aromatics, and other types of hydrocarbon conversion processes.

The ratio of silicon orthophosphate to silicon pyrophosphate may be determined from an integrated X-ray diffraction (XRD) reflectance ratio. This is a comparison of the X-ray reflection intensities generated due to the differing crystallites of these two substances during an XRD experiment. In the catalyst of the invention, the ratio of integrated X-ray diffraction reflectance due to the (113) planes of silicon orthophosphate and the (002) planes of silicon pyrophosphate should be at least about 5:1 and preferably at least about 8:1. This includes the case in which no crystalline silicon pyrophosphate is detected by X-ray diffraction: this would be described as a 1:0 ratio, which is greater than any finite ratio.

The total pore volume and the contribution to the pore volume by pores of various diameters may be obtained from mercury porosimetry. In the inventive catalyst, the total pore volume should be at least about $0.17$ $cm^3$ $g^{-1}$, preferably at least about $0.20$ $cm^3$ $g^{-1}$, and more preferably at least about $0.22$ $cm^3$ $g^{-1}$. The pore volume contributed by pores of diameters of at least about 10,000 Å should be at least about $0.15$ $cm^3$ $g^{-1}$, preferably at least about $0.20$ $cm^3$ $g^{-1}$. It is also preferable that the pores of diameters of at least about 20,000 Å contribute at least about $0.15$ $cm^3$ $g^{-1}$ of the pore volume, and preferable that the pores of diameters at least about 50,000 Å contribute at least about $0.12$ $cm^3$ $g^{-1}$ of the pore volume.

Although the SPA catalyst of this invention may be manufactured in a variety of forms, the preferred form is an extrudate. Extrusion allows the catalyst to be manufactured in various shapes having the requisite pore diameter/pore volume distribution. It is felt that such important properties will be easier to control if the catalyst composite is in extrudate form. Also, extrusion is typically an efficient and cheap method of producing a formed catalyst particle.

The SPA catalyst of the present invention comprises a phosphorus source and a silicon source. The phosphorus source may be any phosphoric acid generally known in the art for use in SPA catalysts. Exemplary phosphorus sources, without limitation, include orthophosphoric acid $H_3PO_4$, pyrophosphoric acid $H_4P_2O_7$, and triphosphoric acid $H_5P_3O_{10}$, and combinations thereof. As is known in the art, the phosphoric acid may further be combined with water. In the inventive catalyst, a phosphoric acid of concentration between about 100% and about 120% is recommended for preparation of the catalyst.

The silicon source may be any siliceous or $SiO_2$-containing material generally known in the art for use in SPA catalysts. Exemplary silicon sources, without limitation, include kieselguhr, diatomaceous earth, infusorial earth, kaolin, fullers earth, artificially prepared porous silica, or mixtures thereof. Kieselguhr is the preferred silicon source.

The solid phosphoric acid catalysts of this invention can be prepared in the following manner. The phosphorus source and the silicon source are mixed at a temperature between about 10° C. and about 232° C., preferably between about 35° C. and about 100° C. This is often done by adding hot phosphoric acid to a silicon source which was kept at room temperature. For example, satisfactory results may be obtained by heating phosphoric acid of phosphorus content of about 110% to a temperature of about 170° C. and then mixing this hot acid with diatomaceous earth which has previously been at room temperature. The mixture resulting from this operation is often called the "green" material (referring to unripeness rather than color) and is referred to as a "dough" or "paste". The dough is slightly moist to almost dry in appearance, but may be extruded in a hydraulic press-type or auger-type extruder or a gear-type pelletizer, and then cut into shaped particles.

Other ingredients, including without limitation additional water, modifiers, binders, cements, or organic material, may be added to the green paste. It is advantageous to add a material which produces gases during calcination, as this aids in the formation of the large pores which characterize this catalyst. Materials which produce gases during calcination include, without limitation, materials such as water or other volatiles which produce gas by evaporation or loss on ignition, and organic or inorganic materials such as those containing starch, cellulose, nitrates, carbonates, oxalates, acetates or other organic salts, polymers, or compounds containing coordinated water or ammonia, which produce gas by decomposition or combustion.

The extrusion step of the catalyst manufacturing process is a factor in determining the porosity of the final catalyst. Extrusion conditions can be optimized to produce the requisite pore volume and the contribution to that volume by pores of large diameter. This especially includes the pore volume due to very large pores with diameters in excess of 10,000 Å. Generally, greater extrusion pressure produces lower porosities, lower pore volumes, and smaller pore diameters in the finished catalysts. Accordingly, excessive extrusion pressure should be avoided. Process variables which influence the extrusion pressure include the force applied by the extruder, the cross-sectional area of the holes in the extruder die plate, the length of the die, and the consistency of the extruded paste. Lower extrusion forces, larger holes in the extruder die plate, shorter die lengths, and moister pastes result in lower extrusion pressure.

The initial, "green" paste formed by mixing the phosphoric acid with the kieselguhr or other silicon source is typically amorphous, and must undergo crystallization to produce the finished SPA catalyst. Crystallization can occur in the period between mixing the ingredients and extrusion, in the period between extrusion and calcination, and during calcination.

The inventive SPA catalysts may be calcined in two or more stages, with each stage having its own time, temperature, oxygen level, and moisture level. For example, the extrudates may be dried at 120° C. for 1 hour in dry air, calcined at 400° C. for 1.5 hours in dry air, and then steamed at 200° C. for 0.5 hours in a 4:1 mixture of air and steam. However, it is not necessary to employ multiple calcination stages: a single stage in which the extrudates are held at a constant temperature for a certain amount of time may also be used.

The calcination temperature and calcination time should be sufficient to ensure growth of the crystalline phases of silicon orthophosphate and silicon pyrophosphate and the desired pore characteristics. Calcination temperatures above 500° C. contribute to excessive formation of silicon pyrophosphate and insufficient formation of silicon orthophosphate. In order to obtain a mixture of silicon orthophosphate and silicon pyrophosphate, the calcination temperature (or highest calcination temperature, if there are multiple calcination stages) should be in the range between about 200° C. and about 500° C., preferably between about 350° C. and about 450° C. Calcination times (total times, if there is more than one calcination stage) will vary depending on other calcination factors, but calcination times between about 20 minutes and about 4 hours are preferred.

The catalyst of the present invention may be used, for example, in the alkylation of aromatic hydrocarbons with olefins to produce alkyl aromatics. In one embodiment, benzene is reacted with ethylene to produce ethylbenzene. In another embodiment, benzene is reacted with propylene to produce cumene. In a typical process, the aromatic hydrocarbon and the olefin are continuously fed into a pressure vessel containing the solid phosphoric acid catalyst of this invention. The feed admixture may be introduced into the alkylation reaction zone containing the alkylation catalyst at a constant rate, or alternatively, at a variable rate. Normally, the aromatic substrate and olefinic alkylating agent are contacted at a molar ratio of from about 1:1 to 20:1 and preferably-from about 2:1 to 8:1. The preferred molar feed ratios help to maximize the catalyst life cycle by minimizing the deactivation of the catalyst by coke and heavy material deposition upon the catalyst. The catalyst may be contained in one bed within a reactor vessel or divided up among a plurality of beds within a reactor. The alkylation reaction system may contain one or more reaction vessels in series. The feed to the reaction zone can flow vertically upwards, or downwards through the catalyst bed in a typical plug flow reactor, or horizontally across the catalyst bed in a radial flow type reactor. A controlled amount of water, in quantities between about 0.01% and about 6% of the combined aromatic and olefin feed, is preferably added to the alkylation reaction zone, in order to prevent dehydration of the catalyst, which affects catalyst performance.

The catalyst in the present invention may also be used in a polygas process. In this process, sometimes called catalytic condensation, olefins in the feed stream are oligomerized to produce heavier hydrocarbons. In an exemplary embodiment, the particles of the catalyst are placed in vertical cylindrical treating towers or in fixed beds in reactors or towers and the gases containing olefins are passed downwardly through the reactors or towers at temperatures of 170° C. to 290° C. and pressures of 6 to 102 atmospheres. These conditions are particularly applicable when dealing with olefin-containing material which may contain from approximately 10 to 50 percent or more of propylene and butylenes. When operating on a mixture comprising essentially propylene and butylenes, preferred process conditions are a temperature from about 140° C. to about 250° C., and at a pressure of from about 34 to about 102 atmospheres.

The following examples are presented to further demonstrate the invention as described herein and are not intended to limit the scope of the invention. For convenience, the catalyst preparation methods are described for each example, and the pore volumes and pore size distribution for the example catalysts are summarized in Table I.

EXAMPLE 1

A sample of 250 g phosphoric acid of 113% concentration is heated to 50° C. To this is added 100 g kieselguhr and 12 g deionized water. The kieselguhr and acid are blended in a high-speed mechanical mixer for several minutes. After blending, the mixture is allowed to cool for 10 minutes. The resulting "green" paste is then extruded using a hydraulic press. The extrudates are calcined in air at 370° C. for 2 hours.

EXAMPLE 2

The procedure of Example 1 is followed, except that the 12 g deionized water is added after the mixing and cooling steps, but before the extruding step.

EXAMPLE 3

A sample of 270 g phosphoric acid of 113% concentration is heated to 45° C. To this are added 100 g kieselguhr and 3 g maize flour. The kieselguhr and acid are blended using a high-speed mechanical mixer for several minutes. After blending, the "green" mixture is extruded using a hydraulic press The extrudates are calcined in air at 320° C. for 30 minutes.

EXAMPLE 4

The procedure of Example 3 is carried out, except that the maize flour content is reduced to 2 g per 100 g kieselguhr.

EXAMPLE 5

The procedure of Example 3 is carried out, except that the maize flour content is reduced to 1 g per 100 g kieselguhr.

EXAMPLE 6

The procedure of Example 4 is carried out, except that the maize flour is replaced by 2 g of wheat flour per 100 g kieselguhr.

EXAMPLE 7

The procedure of Example 4 is carried out, except that the maize flour is replaced by 2 g of sawdust per 100 g kieselguhr.

EXAMPLE 8

The procedure of Example 4 is carried out, except that the maize flour is replaced by 2 g of crushed peanut shells per 100 g kieselguhr.

EXAMPLE 9

A sample of 250 g phosphoric acid of 113% concentration is heated to 45° C. To this is added 100 g kieselguhr which has been dried at 100° C. for 12 hours. The kieselguhr and acid are blended using a high-speed mechanical mixer for several minutes. The resulting "green" material or paste then extruded using a hydraulic press. The extrusions are calcined in air at 370° C. for 2 hours.

The catalysts prepared according to examples 1-9 are subjected to pore volume analysis, with the results appearing in Table 1.

TABLE I

Pore volume in $cm^3/g$ and pore volume contribution by large pores for examples 1-9.

| Example | Total | Pores > 10,000 Å | Pores > 20,000 Å | Pores > 50,000 Å |
| --- | --- | --- | --- | --- |
| 1 | 0.35 | 0.35 | 0.32 | 0.18 |
| 2 | 0.34 | 0.34 | 0.33 | 0.22 |
| 3 | 0.52 | 0.26 | 0.25 | 0.23 |
| 4 | 0.40 | 0.20 | 0.17 | 0.15 |
| 5 | 0.39 | 0.14 | 0.13 | 0.12 |
| 6 | 0.38 | 0.21 | 0.18 | 0.15 |
| 7 | 0.42 | 0.22 | 0.18 | 0.16 |
| 8 | 0.31 | 0.16 | 0.13 | 0.10 |
| 9 | 0.28 | 0.14 | 0.07 | 0.04 |

Catalyst prepared according to examples 3, 4, 5, and 9 are tested under the following conditions. A sample of 100 ml of catalyst pellets is placed in a reactor. A feed containing 55% propylene and 45% propane is passed through the catalyst bed at a linear hourly space velocity of 2.8. The temperature and pressure of the catalyst bed are maintained at 215° C. and 60 bars during the test. The propylene conversion after 24, 48, and 72 hours on stream is given in Table II.

TABLE II

Propylene conversion after 24, 48 and 72 hours on stream.

| Catalyst/ time on stream | Ex. 3 | Ex. 4 | Ex. 5 | Ex. 9 |
|---|---|---|---|---|
| 24 h | 91.1% | 92.7% | 92.9% | 89.1% |
| 48 h | 90.3% | 92.0% | 92.1% | 88.6% |
| 72 h | 89.0% | 90.9% | 91.2% | 88.0% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A solid phosphoric acid catalyst comprising silicon orthophosphate and, optionally, silicon pyrophosphate, having a total pore volume of at least about 0.17 cm$^3$ per gram, of which at least about 0.15 cm$^3$ per gram is due to pores with diameter of at least about 10,000 Å, and having an integrated XRD reflectance intensity ratio of silicon orthophosphate to silicon pyrophosphate which is at least about 5:1.

2. The solid phosphoric acid catalyst of claim 1 wherein said integrated XRD reflectance intensity ratio is at least about 8:1.

3. The solid phosphoric acid catalyst of claim 1 wherein at least 0.20 cm$^3$ per gram of pore volume is due to pores with a diameter of at least about 10,000 Å.

4. The solid phosphoric acid catalyst of claim 1 wherein at least 0.15cm$^3$ per gram of pore volume is due to pores with a diameter of at least about 20,000 Å.

5. The solid phosphoric acid catalyst of claim 1 wherein at least 0.12 cm$^3$ per gram of pore volume is due to pores with a diameter of at least about 50,000 Å.

6. The solid phosphoric acid catalyst of claim 5 wherein said integrated XRD reflectance intensity ratio is at least about 8:1.

7. The solid phosphoric acid catalyst of claim 1 having a total pore volume of at least about 0.22 cm$^3$ per gram of catalyst.

8. A solid phosphoric acid catalyst, prepared from a siliceous material and one or more oxides or oxyacids of pentavalent phosphorus, having a total pore volume of at least about 0.17 cm$^3$ per gram, of which at least about 0.15 cm$^3$ per gram is due to pores with diameter of at least about 10,000 Å, and having an integrated XRD reflectance intensity ratio of silicon orthophosphate to silicon pyrophosphate which is at least about 5:1.

9. The catalyst of claim 8 wherein the siliceous material is chosen from the group consisting of kieselguhr, diatomaceous earth, infusorial earth, and porous silica, and mixtures thereof.

10. The catalyst of claim 9 in the form of a calcined extrudate.

11. The solid phosphoric acid catalyst of claim 9 wherein said integrated XRD reflectance intensity ratio is at least about 8:1.

12. The catalyst of claim 9 wherein at least 0.12 cm$^3$ per gram of pore volume is due to pores with a diameter of at least about 50,000 Å.

13. A process for the conversion of hydrocarbons in the presence of a solid phosphoric acid catalyst by contacting a hydrocarbon feedstock with a solid phosphoric acid catalyst comprising silicon orthophosphate and, optionally, silicon pyrophosphate, having a total pore volume of at least about 0.17 cm$^3$ per gram, of which at least about 0.15 cm$^3$ per gram is due to pores with diameter of at least about 10,000 Å, and having an integrated XRD reflectance intensity ratio of silicon orthophosphate to silicon pyrophosphate which is at least about 5:1, and wherein the conversion of hydrocarbons is an alkylation process or a catalytic condensation process.

14. The process of claim 13 wherein the solid phosphoric acid catalyst has a total pore volume of at least 0.22 cm$^3$ per gram.

15. The process of claim 13 wherein the solid phosphoric acid catalyst has a total pore volume of at least about 0.17 cm$^3$ per gram, of which at least 0.12 cm$^3$ per gram is due to pores with diameter of at least 50,000 Å.

16. The process of claim 13 wherein the catalytic condensation process occurs under hydrocarbon conversion conditions including a temperature between about 140° C. and about 290° C. and a pressure between about 6 atmospheres and 102 atmospheres.

17. The catalyst of claim 8 wherein the total pore volume is at least 0.30 cm$^3$ per gram, wherein at least about 0.10 cm$^3$ per gram is due to pores with diameter of at least about 20,000 Å.

18. The catalyst of claim 8 wherein at least about 0.10 cm$^3$ per gram is due to pores with diameter of at least about 50,000 Å.

* * * * *